(12) United States Patent
Poormand

(10) Patent No.: US 11,786,681 B2
(45) Date of Patent: Oct. 17, 2023

(54) INTUBATION DEVICES

(71) Applicant: Flexicare (Group) Limited, Mid Glamorgan (GB)

(72) Inventor: Ghassem Poormand, London (GB)

(73) Assignee: Flexicare (Group) Limited, Mountain Ash (GB)

( * ) Notice: Subject to any disclaimer, the term of this patent is extended or adjusted under 35 U.S.C. 154(b) by 478 days.

(21) Appl. No.: 16/610,266

(22) PCT Filed: May 2, 2018

(86) PCT No.: PCT/EP2018/061216
§ 371 (c)(1),
(2) Date: Nov. 1, 2019

(87) PCT Pub. No.: WO2018/202720
PCT Pub. Date: Nov. 8, 2018

(65) Prior Publication Data
US 2020/0297957 A1 Sep. 24, 2020

(30) Foreign Application Priority Data
May 5, 2017 (GB) ..................................... 1707174

(51) Int. Cl.
*A61M 16/04* (2006.01)
*A61M 16/06* (2006.01)

(52) U.S. Cl.
CPC ...... *A61M 16/0418* (2014.02); *A61M 16/045* (2014.02); *A61M 16/0463* (2013.01);
(Continued)

(58) Field of Classification Search
CPC ............ A61M 16/0418; A61M 16/045; A61M 16/0463; A61M 16/0488
See application file for complete search history.

(56) References Cited

U.S. PATENT DOCUMENTS

| 4,207,873 A | 6/1980 | Kruy |
| 4,880,015 A | 11/1989 | Nierman |

(Continued)

FOREIGN PATENT DOCUMENTS

| WO | WO 90/01964 A1 | 3/1990 |
| WO | WO 2006/039016 A1 | 4/2006 |

(Continued)

OTHER PUBLICATIONS

PCT International Search Report dated Jun. 18, 2018 in related PCT Application No. PCT/EP2018/061216.
(Continued)

*Primary Examiner* — LaToya M Louis
(74) *Attorney, Agent, or Firm* — Robert D. Buyan; Stout, Uxa & Buyan, LLP

(57) ABSTRACT

A stylet is disclosed for insertion into an endotracheal tube for guiding the tube during intubation. The stylet has a body (3) with a pivotable tip portion (5) at its distal end which is movable in either of two opposing directions away from the axis of the stylet. The tip portion (5) may carry an image acquisition device for video imaging. A control mechanism for controlling the pivot angle of the pivotable tip has a hand-operated actuator (7) at the proximal end of the stylet and flexible control wires (23) extending down the stylet to connect the actuator to the pivotable tip portion (5). Also disclosed is an endotracheal tube (100) usable with the stylet and having a bending portion (103), defined by a concertina or thinned portion, at its distal end to facilitate bending of its tip portion (104) by the stylet tip portion (5).

36 Claims, 9 Drawing Sheets

(52) U.S. Cl.
CPC .... *A61M 16/0488* (2013.01); *A61M 16/0672*
(2014.02); *A61M 2205/583* (2013.01)

(56) References Cited

U.S. PATENT DOCUMENTS

| | | | |
|---|---|---|---|
| 5,549,542 | A | 8/1996 | Kovalcheck |
| 5,645,519 | A | 7/1997 | Lee et al. |
| 5,791,338 | A | 8/1998 | Merchant et al. |
| 5,842,973 | A | 12/1998 | Bullard |
| 5,976,075 | A | 11/1999 | Beane et al. |
| 6,432,042 | B1 | 8/2002 | Bashour |
| 8,505,531 | B2 | 8/2013 | Pecherer et al. |
| 8,746,239 | B2 * | 6/2014 | Yoshida ................ A61M 16/04 128/207.14 |
| 9,949,629 | B2 | 4/2018 | Gardner |
| 10,368,726 | B2 | 8/2019 | Perez-Lizano |
| 11,617,498 | B2 | 4/2023 | Perez-Lizano |
| 2002/0096177 | A1 | 7/2002 | Toti et al. |
| 2003/0069565 | A1 | 4/2003 | Miser |
| 2004/0044350 | A1 | 3/2004 | Martin et al. |
| 2005/0182297 | A1 | 8/2005 | Gravenstein et al. |
| 2007/0219499 | A1 | 9/2007 | Hayakawa et al. |
| 2008/0236575 | A1 * | 10/2008 | Chuda ................ A61B 1/00052 128/200.26 |
| 2010/0094090 | A1 * | 4/2010 | Mejia ................ A61B 1/00052 600/156 |
| 2011/0120458 | A1 * | 5/2011 | Schwartz ............... A61B 1/267 128/200.26 |
| 2011/0265789 | A1 | 11/2011 | Gabriel |
| 2012/0022326 | A1 | 1/2012 | Jaime |
| 2012/0055470 | A1 | 3/2012 | Pecherer et al. |
| 2012/0078056 | A1 | 3/2012 | Tenger et al. |
| 2013/0035548 | A1 * | 2/2013 | Ianchulev .......... A61B 1/00052 128/200.26 |
| 2014/0041665 | A1 | 2/2014 | Hwang |
| 2014/0123976 | A1 * | 5/2014 | Mccormick ....... A61M 16/0488 128/200.26 |
| 2015/0096556 | A1 * | 4/2015 | Marks ............... A61M 16/0488 128/207.14 |
| 2015/0099935 | A1 | 4/2015 | Runnels |
| 2015/0366445 | A1 * | 12/2015 | Rutgers ................ A61B 1/2676 128/200.26 |
| 2016/0038001 | A1 | 2/2016 | Perez-Lizano |
| 2016/0058267 | A1 | 3/2016 | Petersen et al. |
| 2018/0318534 | A1 | 11/2018 | Desatnik et al. |

FOREIGN PATENT DOCUMENTS

| | | | |
|---|---|---|---|
| WO | WO 2007/138569 | A1 | 12/2007 |
| WO | WO 2011/119521 | A1 | 9/2011 |
| WO | WO 2014/123473 | A1 | 8/2014 |
| WO | WO 2017/123941 | A1 | 7/2017 |
| WO | WO2018/005776 | A2 | 1/2018 |
| WO | WO 2018/075797 | A1 | 4/2018 |

OTHER PUBLICATIONS

United Kingdom Search Report dated Oct. 19, 2018 in related United Kingdom Application No. GB1707174.7.
Third Party Observation for Application No. EP20180721384 dated May 18, 2023.
Paul A. Kvale, Md, "The Flexible Bronchoscope: Which Hand Should Hold It? Pro: Left Hand," J. Bronchol, vol. 10, No. 4, Oct. 2003.
Third Party Observation for Application No. EP20180721384 dated Apr. 4, 2023.
Simon Prior, et al., "Parker Flex-Tip and Standard-Tip Endotracheal Tubes: A Comparison During Nasotracheal Intubation," Anesth Prog 57:15-24, 2010.
Office Action dated May 13, 2022 in corresponding European Patent Application No. 18721384.8.
Office Action dated Feb. 6, 2023 in corresponding European Patent Application No. 18721384.8.
Third Party Observation for Application No. EP20180721384 dated Nov. 29, 2022.
Third Party Observation for Application No. EP20180721384 dated Dec. 4, 2022.
Third Party Observation for Application No. EP20180721384 dated Dec. 5, 2022.
Third Party Observation for Application No. EP20180721384 dated Feb. 11, 2023.
Third Party Observation for Application No. EP20180721384 dated Feb. 13, 2023.
Third Party Observation for Application No. EP20180721384 dated Feb. 20, 2023.
Third Party Observation for Application No. EP20180721384 dated Feb. 21, 2023.
Third Party Observation for Application No. EP20180721384 dated Mar. 27, 2023.

* cited by examiner

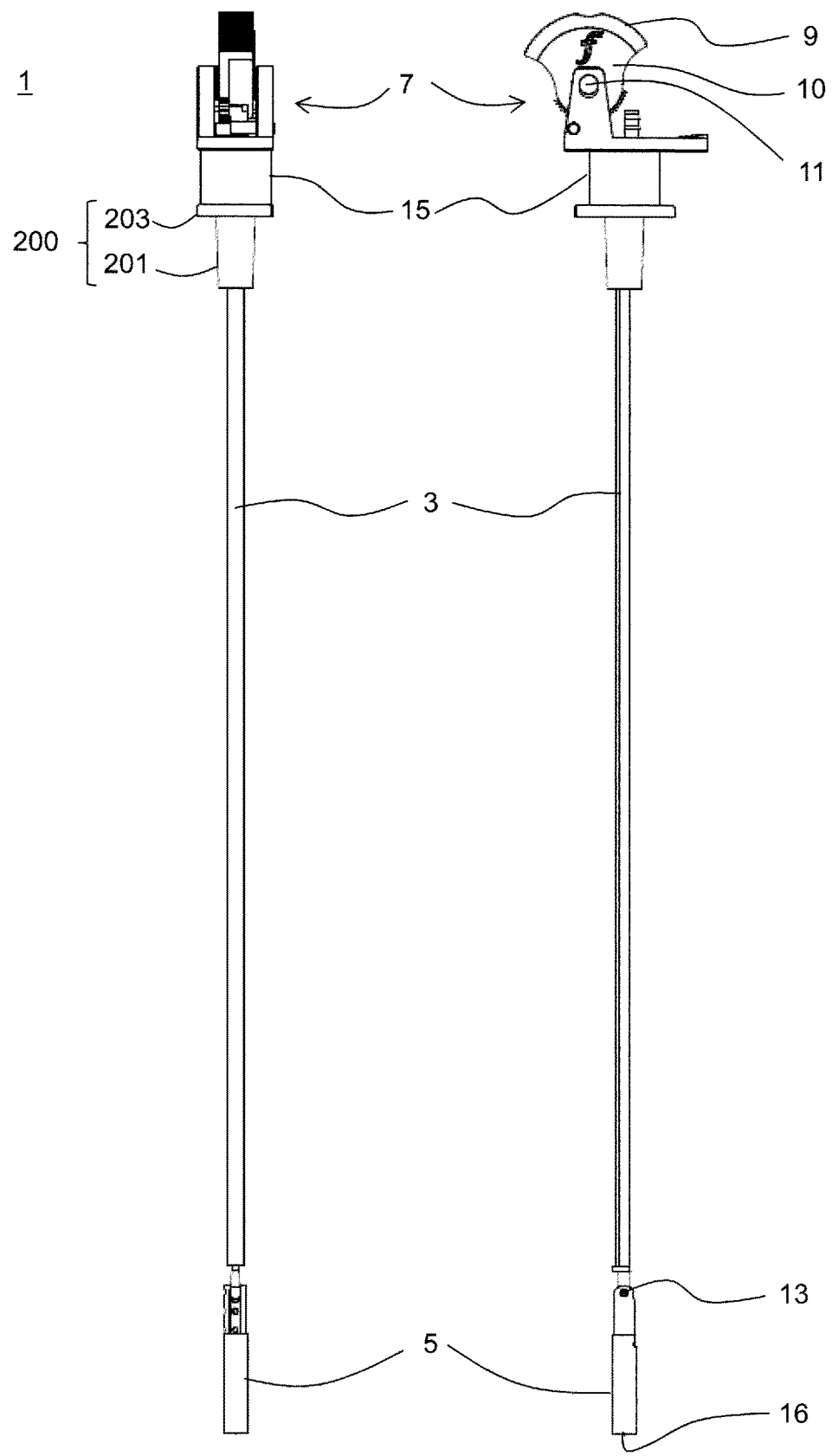

Fig. 5
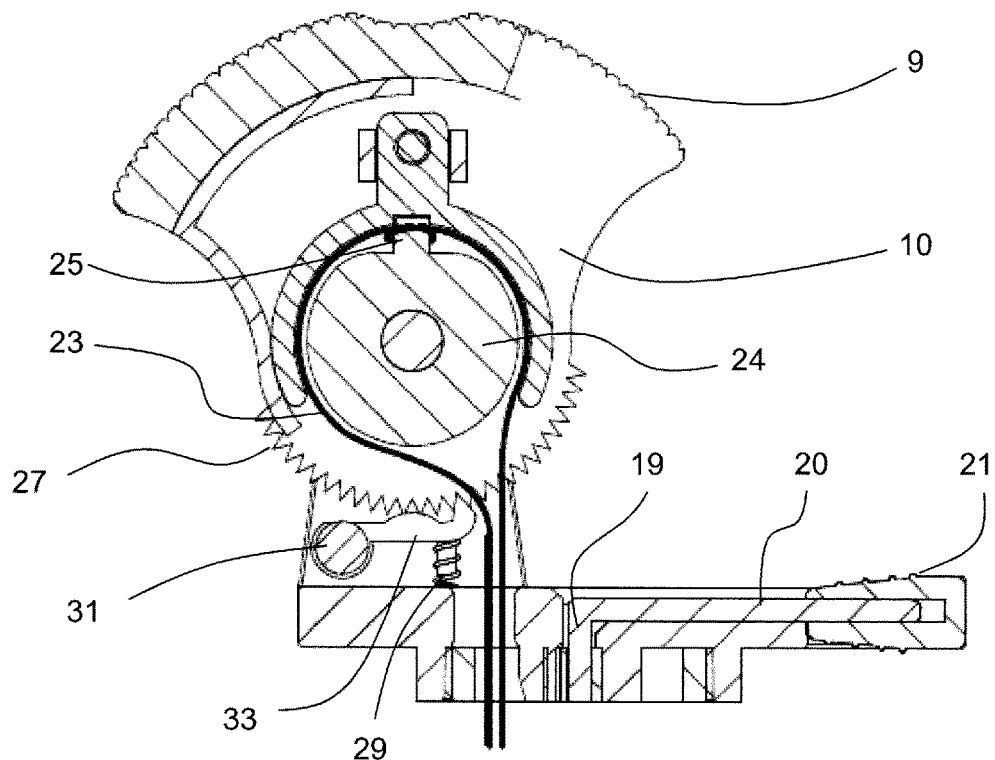
Fig. 6(a)    Fig. 6(b)
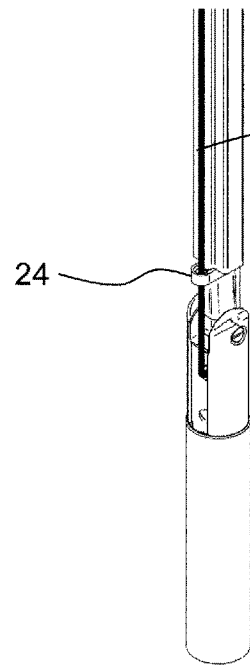
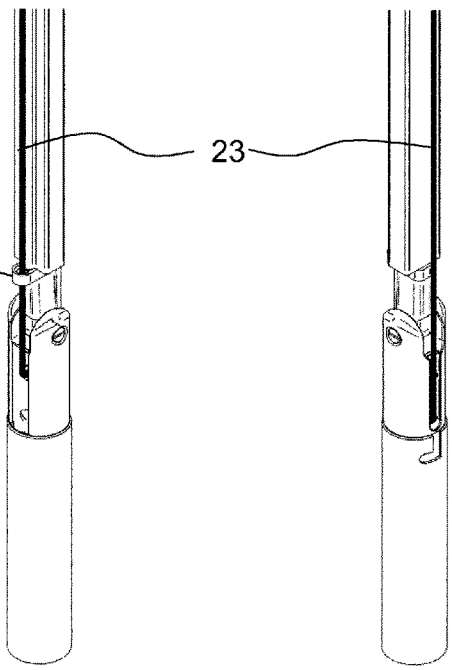

Fig. 7 (a)      Fig. 7 (b)      Fig. 7 (c)
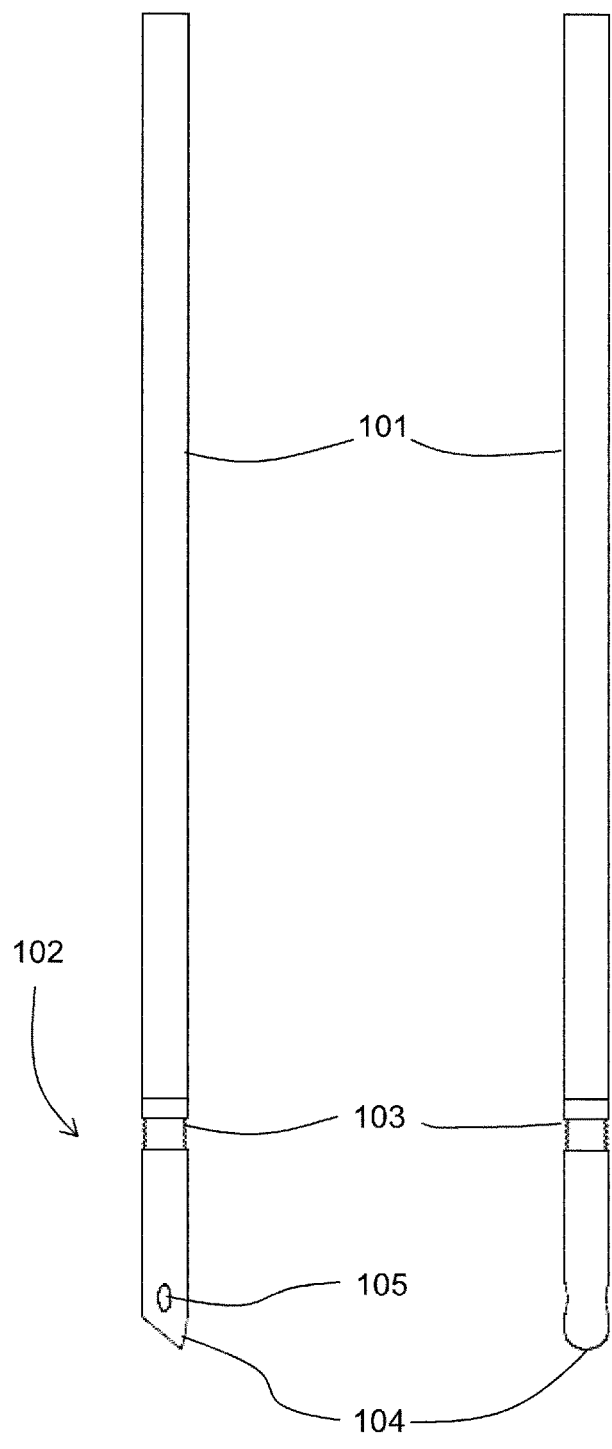
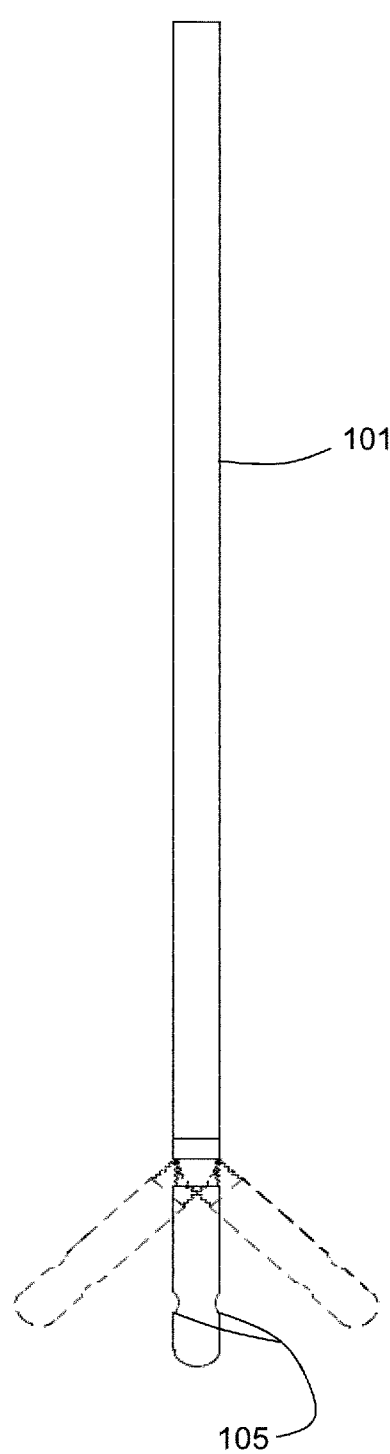

Fig. 9
Fig. 10
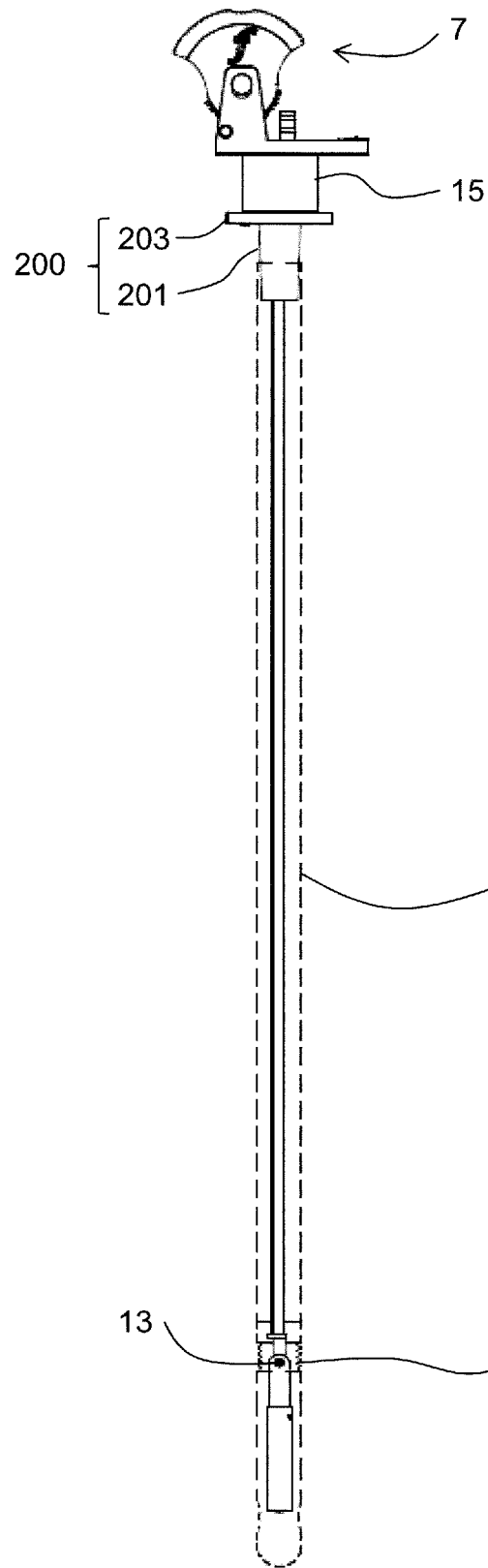
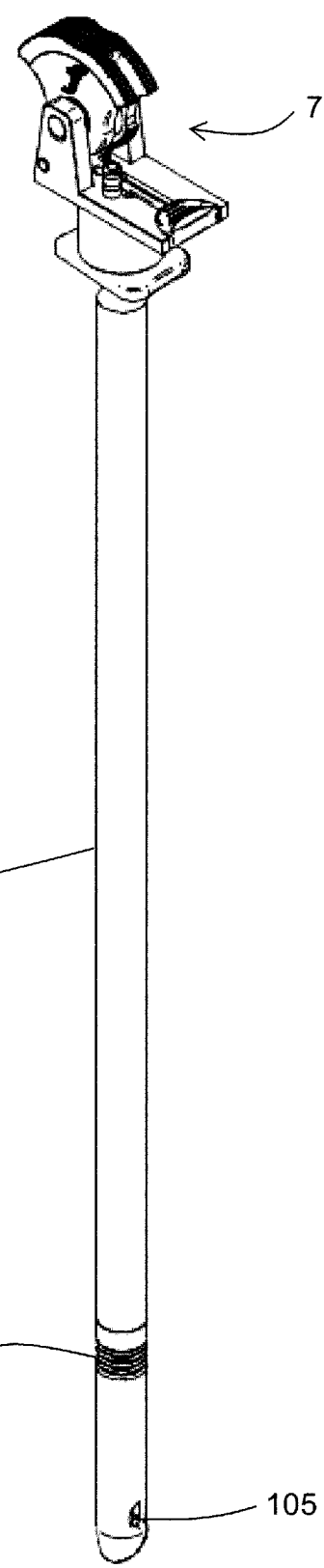

INTUBATION DEVICES

RELATED APPLICATIONS

This patent application is a national stage filing under 35 U.S.C § 371 of Patent Cooperation Treaty International Application No. PCT/EP2018/061216, filed May 2, 2018 entitled Intubation Devices, which claims the benefit of and right of priority to United Kingdom patent application GB1707174.7 filed May 5, 2017 and subsequently published as GB-A-2563567, the entire disclosures of each such application being expressly incorporated herein by reference.

FIELD OF THE INVENTION

The present invention relates to intubation devices. In particular, it relates to endotracheal tubes, and style's for use with endotracheal tubes.

BACKGROUND

During tracheal intubation, an endotracheal tube (ET tube) must be inserted into a patient's airway. In a typical intubation process a clinician standing above/behind the head of the supine patient will use a laryngoscope to move the tongue and epiglottis out of the way and then insert an ET tube through the patient's vocal cords into the trachea. Once the ET tube is correctly positioned in the trachea, commonly a cuff on the ET tube will be inflated to hold the tube in position for ventilation of the patient. It is necessary to ensure accurate placement of the ET tube in the trachea and to avoid incorrect placement of the ET tube e.g. into the oesophagus rather than into the trachea. The patient is commonly anaesthetised and apnoeic, so the intubation procedure has to be completed rapidly, and it is advantageous to confirm correct placement of the ET tube quickly and accurately so that ventilation can begin.

Location of the ET tube can be determined using a number of methods, including visualisation, capnography, and X-ray location of the tube, alongside physical examination methods such as auscultation of the chest and epigastrium, and visualisation of thoracic movement. However, many of these methods of determining ET tube placement are not sufficiently reliable to be used as sole techniques to correctly determine ET tube location. Direct visualisation of the ET tube passing through the vocal cords into the trachea is the most reliable method of quickly and accurately determining correct placement of the ET tube.

In some cases, the clinician performing the intubation may be able to directly visualise placement of the ET tube, but this is not always possible, depending on the particular anatomy of the patient. For example difficulties may be encountered where the patient has restricted neck flexibility, or is obese. For such patients, video laryngoscopes are a well-known option for facilitating intubation. However, video laryngoscopes can have drawbacks. The video apparatus is typically provided at an intermediate location along the laryngoscope blade, the distal end of the blade can partially obstruct the field of view. Also the ET tube itself may obstruct the view of the vocal cords and trachea as it advances past the end of the laryngoscope. Video laryngoscopes tend to be expensive, which further limits their use as single use devices.

The act of placing the ET tube offers its own difficulties, even when it can be visualised clearly. Typically an ET tube is made from semi-rigid polymer, and has a gentle curve to align with the airways of the patient. However, patient anatomy may require that the ET tube has a specific shape, for example, a sharper bend at the distal end, to aid insertion through the vocal cords into the trachea. Because the material of the ET tube is generally flexible and does not retain shape when bent, a stylet may be used with the ET tube. A stylet is an elongate device inserted into an ET tube to hold it in a specific—perhaps altered—shape to facilitate intubation. Stylets may also provide additional rigidity to the ET tube to aid navigation of the ET tube into the desired location. Some known stylets can be inserted into the ET tube and shaped by the clinician so the form of the ET tube is retained before and during insertion of the combined devices into the patient's airway. However setting the shape of the stylet before intubation can lead to undesirable delays during the intubation procedure where the set shape turns out to be not quite right for the patient's anatomy.

To overcome one or more of the above problems, stylets which offer adjustability during the intubation procedure have been proposed. For example US-A1-2016/0038001 proposes a stylet which may be flexed along its length by application of opposing forces to two pressure receiving elements at the proximal end of the stylet, and which also has imaging and display capabilities.

THE INVENTION

An aim herein is to provide new and useful intubation devices which can aid accurate visualisation and placement of endotracheal (ET) tubes during intubation.

In a first aspect, the invention provides a stylet for guiding an endotracheal tube during intubation. The present invention includes a number of individual proposals relating to various features of a stylet, each of which may be considered individually or in combination with any other of the proposals herein.

One proposal herein is that the stylet comprises a body having a pivotable tip located at a distal end of the body. Pivotable refers to the fact that the tip pivots at a defined pivot point. By allowing the tip to pivot at a pivot point, rather than providing gradual bending along a deflectable portion of the stylet, it is possible to accurately adjust the direction of the stylet tip, without affecting the shape of the rest of the stylet body by e.g. additional unwanted bending along the length of the stylet. Preferably, the pivotable tip is rigid, and affixed to the distal end of stylet body at a pivot hinge. The pivot angle of the tip is defined as the angle between the longitudinal axis of the distal end of the stylet body, and the longitudinal axis of the tip. The pivotable tip is pivotable in two opposing directions relative to the direction of the longitudinal axis of the distal end of the stylet body, and/or relative to a neutral or rest position of the tip. This pivot range of the tip may be at least ±10°, preferably at least ±20° or more preferably at least ±30°, to allow a degree of deflection suitable for guiding the end of an ET tube into the desired location. The range of movement of the tip may or may not be symmetrical, of course. A range of at least ±10° therefore includes a tip which is movable between, e.g. −10° and +15°.

The pivot range of the tip may as large as ±45°, ±50°, ±60°, ±70°, ±80° or ±90° from the longitudinal axis of the distal end of the stylet body. A pivot range of ±90° from the longitudinal axis of the distal end of the stylet body means that the tip can pivot through a 180° pivot range, from a position substantially perpendicular to the distal end of the stylet body on one side of the body (−90°), through a position substantially parallel to the longitudinal axis of the distal end of the stylet body (0°), to a position substantially perpendicular to the distal end of the stylet body on the opposing side of the stylet body (+90°). Advantageously, the stylet allows for movement of the stylet tip through a wider range of motion than typical known stylets. Furthermore, more accurate control of the distal end of the ET tube into which the stylet in inserted during an intubation procedure can be achieved.

Another proposal herein also relates to a stylet tip portion which can be deflected from a rest or neutral position relative to the stylet body, especially at a local flexure portion between the body and tip portion such as a pivot, such as in the first proposal above. The tip deflection is controlled by a control mechanism having an actuator. The actuator may be disposed at a proximal end of the stylet body, for ease of access by a clinician during an intubation procedure. The actuator may comprise a rotatable, pivotable or slidable control portion. For example, it may comprise a wheel, dial, lever or joystick. Preferably the actuator of the control mechanism is hand-operated, however various electronically-controlled mechanisms are also contemplated. For example, where the actuator comprises a rotatable control portion, this could be connected to a motor for driving rotation of the control portion, the motor being controlled by an electronic control module.

The actuator is connected to the pivotable tip by one or more control connectors, typically flexible lines such as wires (henceforth "wires"). Preferably, there is at least a first portion of wire connected to one side of the pivotable tip, and a second portion of wire connected to the opposing side of the tip. In this way, by applying tension to the first wire portion, the tip can be moved in a first direction. By applying tension to the second wire portion, the tip can be moved in a second direction. The first and second wire portions may be part of a single piece of wire. Alternatively, the first and second wire portions may be two separate wires.

Preferably, the control mechanism provides a plurality of discrete predetermined stop points for the actuator. For example, the actuator may include first and second relatively moveable members, wherein the first member has e.g. a series of notches which act as discrete stop points by engagement with a portion of the second of the relatively moveable members. Preferably, the first relatively moveable member is a rotatable control portion having a series of notches which sequentially engage with a detent of the second relatively moveable member as the control portion is rotated. These stop points can provide locking of the pivotable tip at discrete incremental pivot angles. By providing discrete stop points, a person operating the control mechanism can set the pivot angle of the tip to a particular angle, and keep the tip locked at this angle without further interaction by the operator; the operator may let go of the actuator. This is advantageous in comparison to known systems which require that the control mechanism is continuously held at the correct position to give the desired stylet shape. The stop points may provide incremental pivot angle changes of between 1° and 20°. For example, the stop points may provide incremental pivot angle changes of 1°, 2°, 5°, 10° or 15°.

Where the second relatively moveable member has a detent, the detent may be moveable to allow it to move into and out of engagement with notches on the first relatively movable member. Preferably, the first and second members are biased into engagement e.g. of one or more detents with one or more notches. Conveniently, one or both members e.g. member having the detent, may be attached to a spring member which acts to urge the detent into engagement with the notches. The detent may preferably be shaped to help prevent jamming of the actuator. For example, the detent may have a protrusion which restricts the distance the detent can enter into the notches on the first relatively moveable member. Preferably the detent is pivotable, and can pivot into and out of engagement with the notches.

The actuator may have one or more end stops which restrict a movement range of the actuator and correspondingly the pivot range of the pivotable tip. Providing such an end stop can prevent over-bending of the tip, which may be desirable to prevent damage to the stylet and/or the endotracheal tube. The end stops may be formed as part of a sliding arrangement. For example, the end stops may be formed as end stops of a groove in which a pin slides. One proposed configuration includes a recessed slot formed in the dial of the actuator, into which a pin projecting from the actuator body is located. On rotation of the dial, the pin slides along the slot until it reaches an end stop at one end of the slot, thereby preventing further rotation of the dial, and corresponding movement of the tip. The skilled person will be aware of a range of other suitable configurations which would be suitable for restricting the movement range of the actuator. For example, a simple modification of the above proposed configuration is the pin may be formed on the dial, and the slot may be formed on the actuator body.

Another proposal is that the stylet may have an image acquisition device disposed on the pivotable tip. Preferably the image acquisition device is disposed at the distal end of the tip portion, and is arranged to capture images in a direction along the longitudinal axis of the tip, distal to the tip. Where the stylet is used in combination with an ET tube, the image acquisition device may be arranged to capture images from the end of the ET tube. However, it is contemplated that for some uses, the image acquisition device may be arranged to capture images in a direction radial to the longitudinal axis of the stylet. Providing an image acquisition device in the stylet has a number of benefits. Because of the wide range of movement of the stylet tip, locating an image acquisition device in the tip offers a large possible field of view. The tip can be adjusted as desired to better capture the desired field of view. Furthermore, because the stylet will typically be located within the ET tube during intubation, placement of the image acquisition device at the stylet tip allows for visualisation of the vocal cords and trachea of a patient as the ET tube passes through the vocal cords. Accordingly, correct placement of the tube can be reliably determined with minimal obstruction to the field of view.

The term "image acquisition device" refers to means for acquiring an optical image for transmission via electronic signal. For example, the image acquisition device may be a digital image sensor including a charge coupled device (CCD). The images acquired may be one or more still images, or may be video footage. The skilled person will be well aware of a wide range of image acquisition devices which would be suitable for use in the present invention.

The stylet may comprise a preforming rod removably disposed within a lumen of the stylet body. Typically the stylet body is tubular with a central lumen. Such preforming rods are known as such and are of material and dimensions selected for ready plastic deformation. Providing a preforming rod allows a clinician to bend the stylet into a desired shape to assist with intubation. However, the rod is removable to facilitate certain procedure such as nasal intubation, intubation through an intubating oropharyngeal airway, or intubation through a supraglottic airway device. The rod may have a rectangular cross section, which can increase the stylet's resistance to torsion, however this is not essential, and rods with other cross sections, (e.g. square, circular or otherwise) may also be used. An oblong cross section is desirable to promote preferential bending in a single plane. The material of the preforming rod may be of a malleable material such as metal (which may be metal alloy), as is known, for example, titanium, aluminium, or steel. Preferably, the rod is made of titanium. The rod may be substantially the same length as the stylet body. Conveniently, the rod may have a handle at the proximal end to increase ease of insertion and/or removal of the rod from the lumen of the stylet body. The handle portion may have a textured (e.g. ridged) gripping portion to further assist in insertion/removal of the rod from the lumen of the stylet body.

Another proposal is that the stylet may have an attaching portion located at a proximal end of the stylet body, adapted for attachment to an ET tube connector. ET tube connectors are well-known in the art, and are used to connect an ET tube to ventilation apparatus. Typically, they will be a single component having a tapered portion for removable insertion into an ET tube, a flange to aid grip, and a ventilation attachment portion for attaching to the ventilation apparatus.

Preferably, the attaching portion of the stylet is adapted to connect to the ventilation attachment portion of an ET tube connector. The attaching portion of the stylet may therefore be a plug portion adapted to provide a plug fit connection to the corresponding ET tube connector. Accordingly, with this configuration, the stylet can be attached to an ET tube via attachment to an ET tube connector. This is not essential, but is advantageous, as it helps to prevent relative longitudinal movement of the stylet with respect to the ET tube during intubation, and can additionally help to prevent the stylet from protruding from the distal end of the ET tube during intubation, which may be undesirable as such protrusion can cause damage to the patient's airways. Preferably, the attaching portion is integral with a body or retaining housing of the actuator of the stylet.

The stylet may have a port for connection to an oxygen line. Preferably, the port passes through a body or retaining house of the actuator of the control mechanism, into a space defined by an attaching portion of the stylet. Such a configuration can allow oxygen to be delivered directly into an ET tube to which the stylet is connected via an ET tube connector.

In a second aspect, we propose an endotracheal tube (ET tube) which is particularly suitable for use with stylets of the type proposed above, but which may also be used in combination with other stylets.

General features of an ET tube include the following, which may be used in our proposals and are familiar to the skilled person. This means that a clinician using the ET tube will be familiar with the overall configuration of the ET tube, which is helpful for successful intubation in the limited time available. Accordingly, the ET tube has a body comprising a flexible, hollow tube having a distal end for insertion into a patient's trachea during intubation, and a proximal end, which the clinician may hold and use to direct movement of the distal end of the tube. The proximal end is typically attached to an ET tube connector for connection of the ET tube to ventilation apparatus after the intubation procedure has been completed. The ET tube connector may be removable so that it can be removed to allow the ET tube to be cut to length after insertion, and then subsequently replaced to allow connection of the ET tube to ventilation apparatus.

The tube may have an inflatable cuff which can be inflated during the intubation procedure once the ET tube is in place, to hold the tube in the correction position to protect from pulmonary aspiration, and permit positive presume ventilation of the patient. Where the tube has an inflatable cuff, this is connected to an inflation line through which air may be pumped to inflate the cuff. At least a portion of the inflation line may be recessed into the wall of the ET tube.

The distal end of the tube may have a bevelled tip, to aid in insertion of the tube between the vocal cords of the patient. Typically, the distal end of the tube will also have a subsidiary opening to provide an alternate gas passage in the case of occlusion of the main opening, e.g. an opening known as a Murphy eye formed in a sidewall of a tip portion of the tube.

One proposal herein is that the ET tube may have multiple such subsidiary air openings, for example two Murphy eyes. The openings may be formed in opposing sidewalls of a distal tip portion of the ET tube. Where there are multiple openings, they can be smaller whilst retaining the same total flow area for the passage of gas in comparison to typical known tubes having only one Murphy eye. The advantage of providing multiple, smaller openings or Murphy eyes is that it can prevent a stylet tip from passing through or catching in these openings.

A proposal herein is that an ET tube has a bending portion or local flexure at the distal end of the tube. A bending portion is a portion of the tube which is more susceptible to bending under a bending force than the body of the ET tube. The bending portion may extend out to the distal tip of the ET tube. Alternatively, the bending portion may be a portion at the distal end region of the ET tube, but intermediate the body and a less flexible distal tip portion of the tube. The exact location and length of the bending portion will depend on a number of factors, as discussed below. Preferably, the position of the bending portion is selected to align with the expected position of the pivot point of the pivotable tip of the stylet of the first aspect when the stylet and ET tube are used together.

The bending portion may be a concertina portion, i.e. with one or more wall corrugations to enable easier flexing at that portion. Alternatively or additionally, the bending portion may be a portion made from a different material to the material of the body of the ET tube. The bending portion may be locally thinned in comparison to the thickness of the body of the tube. Each of these features, which may be used separately or in combination, can make the bending portion more susceptible to bending than the body of the ET tube. Accordingly, when used in combination with a stylet of the first aspect of the present invention, the distal end of the ET tube may be easier to direct by control of the pivotable tip of the stylet. This can allow the ET tube to be more easily guided into the correct location by the clinician.

In a third aspect, we propose an intubation kit, including a stylet in combination with an endotracheal tube. The kit may include a stylet of the first aspect and/or an endotracheal tube of the second aspect.

The kit can be used to perform an intubation process by a) inserting the stylet into the ET tube, b) inserting the stylet and ET tube into the airway of a patient, c) visualising the airway of the patient, preferably using an image acquisition device of the stylet, d) guiding the ET tube and stylet through the vocal cords of the patient into the trachea, and e) removing the stylet from the ET tube. Such a kit can offer increased ease of intubation, in particular for patients with difficult airways.

An intubation method using the present stylet, ET tube or intubation kit is a further aspect of our proposals.

BRIEF DESCRIPTION OF THE DRAWINGS

Embodiments of the invention will now be described by way of example with reference to the accompanying drawings in which:

FIG. 1 shows (a) a front aspect, and (b) a side aspect of a stylet;

FIG. 5 is a sectional view of the actuator of FIG. 3;

FIGS. 6 (a) and (b) show two different perspective views of the pivotable tip of a stylet;

FIG. 7 shows (a) a side aspect and (b) a front aspect of a first embodiment of an ET tube, and further shows (c) a side aspect showing bending of the bending portion of the ET tube;

FIG. 9 shows a schematic view of an intubation kit;

FIG. 10 is a perspective view of the kit, and

DETAILED DESCRIPTION, FURTHER OPTIONAL FEATURES

Figure 2A:
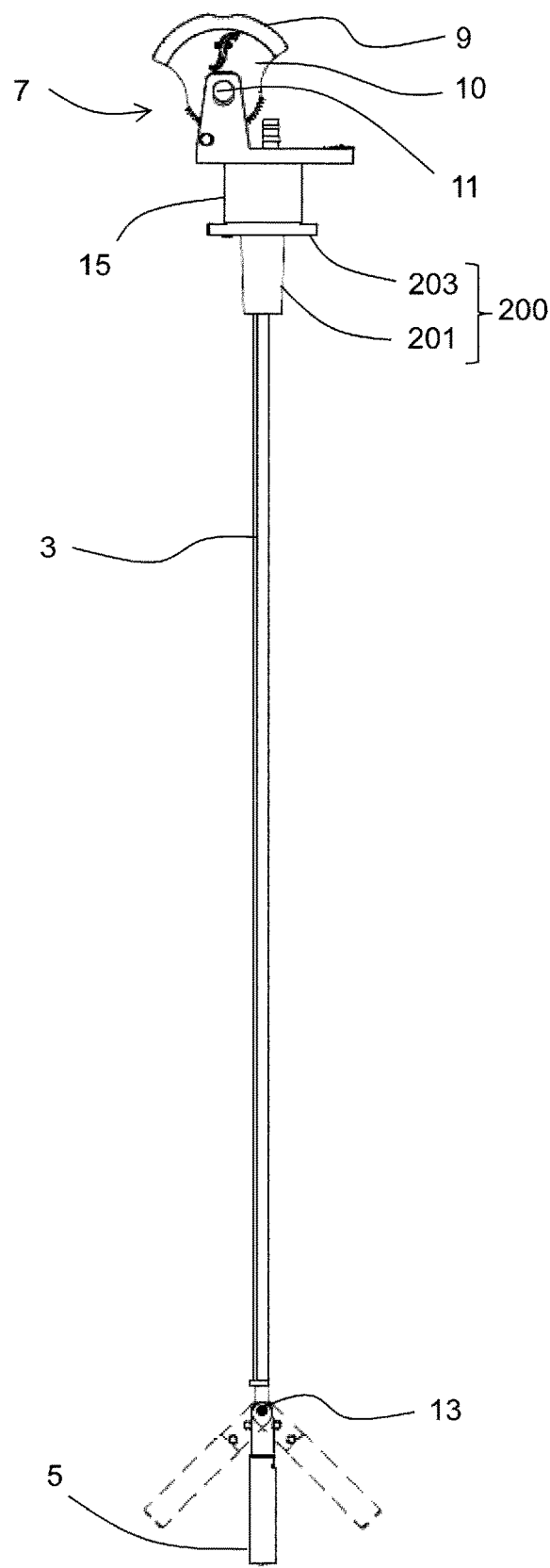
FIG. 2 shows (a) a side aspect of a stylet showing movement of the pivotable tip, and (b) a detail view of the pivotable tip showing the pivot angle of the tip.

FIG. 1 shows (a) a front aspect, and (b) a side aspect of a stylet 1 embodying our proposals, connected to an ET tube connector 200. The stylet has a stylet body 3 with a distal and a proximal end. Distal and proximal are here described in relation to the use of the stylet, with the proximal end being the end of the stylet which is typically held by an operator during use in a process of intubation. The distal end of the stylet is the end which in use may be inserted into a patient's airway to assist in an intubation process. The stylet has a pivotable tip 5 located at the distal end of the stylet body, and an actuator 7 attached at the proximal end of the stylet body. The actuator (shown in FIG. 3 and described in detail below) is here conveniently manipulated by the operator using a thumb-pad 9 on a dial 10 which rotates around an axle 11. The pivotable tip is affixed to the stylet body 3 at a pivot hinge 13 which allows movement of the pivotable tip in a plane. The stylet has an attaching portion 15 located at the proximal end of the stylet, formed integrally with the body/retaining housing 17 of the actuator. The attaching portion here is formed as a receiving socket or plug portion which forms a plug-fit connection with an ET tube connector 200, which has a tapered portion 201 for connecting to an ET tube, and a flange portion 203. The ET tube connector 200 is one of standard known ET tube connectors and does not in itself form part of the proposals relating to the stylet. The stylet has an image acquisition device 16 disposed at the end of the tip. This device is therefore positioned in such a way as to be able to capture images distal to the distal tip of the stylet. Where the stylet is used in combination with an ET tube, the image acquisition device will therefore capture images from the end of the ET tube. The images captured by the device may be transmitted in real time to a display device. Conveniently, there may be a wire (not shown) running along or inside the body of the stylet for electronically transmitting the image(s) from the image acquisition device at the stylet tip to such a display device. Where there is such a wire, it may be protected by a sheath. Other method of transmitting such images are also contemplated, including, for example, wireless transmission of image data.

Figure 2B:
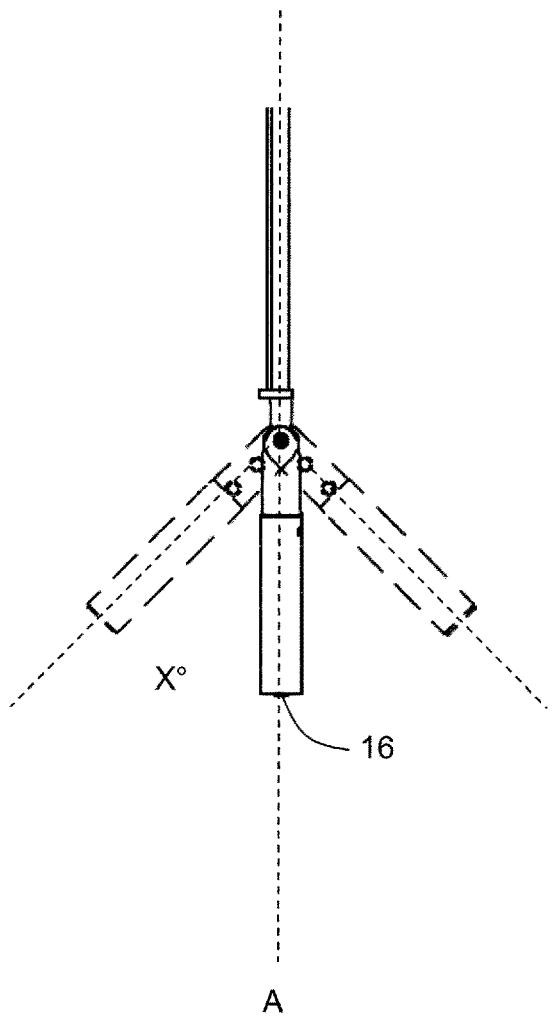

FIGS. 2 (a) and (b) show the range of movement of the pivotable tip in this stylet. The tip can pivot at the pivotable hinge within a pivot range ±X° from the longitudinal axis of the distal end of the stylet body, marked as axis A in FIG. 2 (b). In FIG. 2 (b) the pivot range is observed to be approximately ±45°, however depending on the exact configuration of the stylet, a pivot range of up to ±90° may be possible. Advantageously, the tip can pivot in both directions from a 'neutral' position where the tip is generally aligned with the stylet body. Accordingly, the stylet offers improved manoeuvrability of the stylet tip which can assist in more accurate guiding of an ET tube during an intubation process. The mechanism by which the pivoting of the tip is controlled is discussed in relation to FIGS. 3-5, below.

Figure 3:
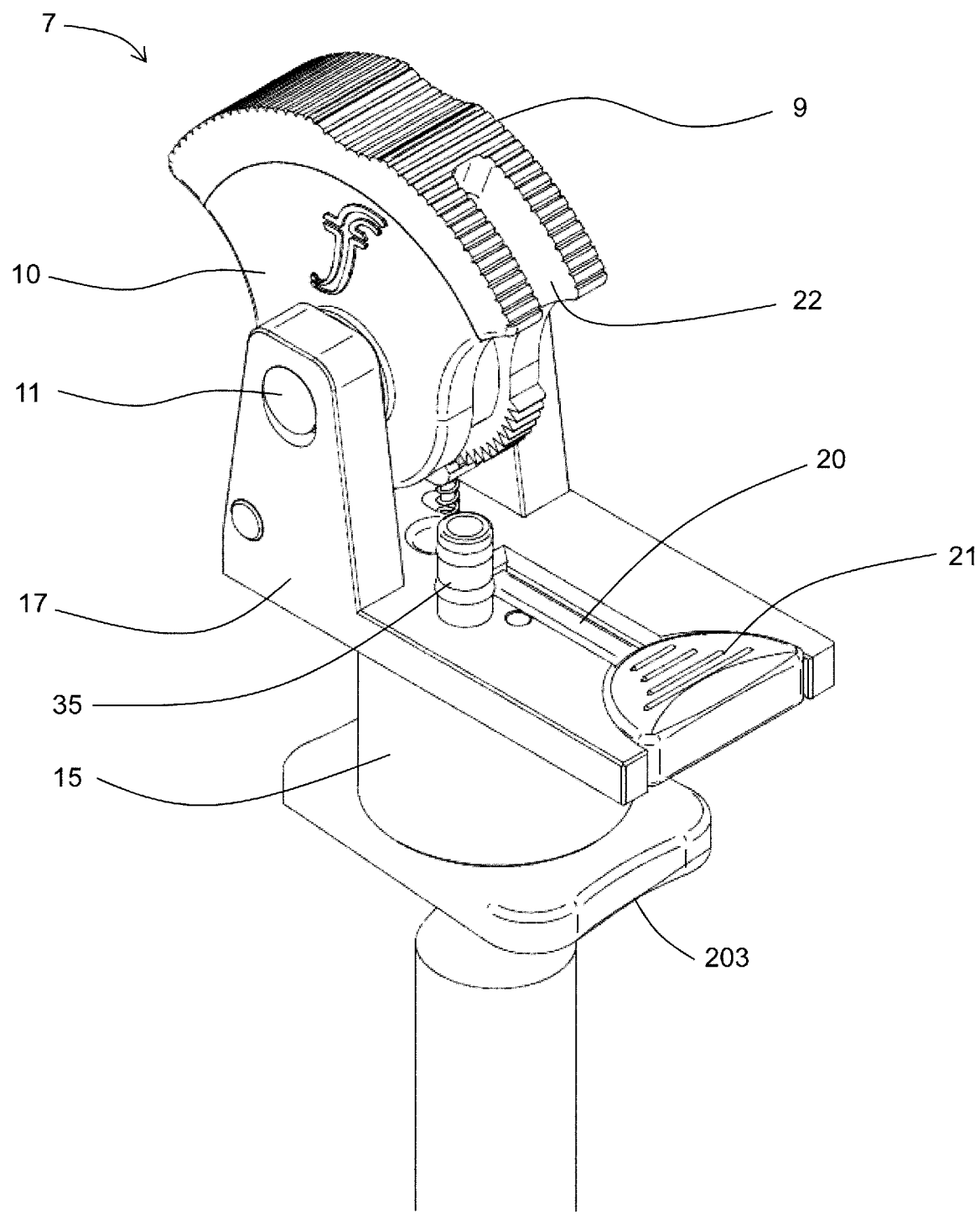
FIG. 3 shows a perspective view of an actuator of the stylet of FIGS. 1 and 2 (control wire omitted)
Figure 4:
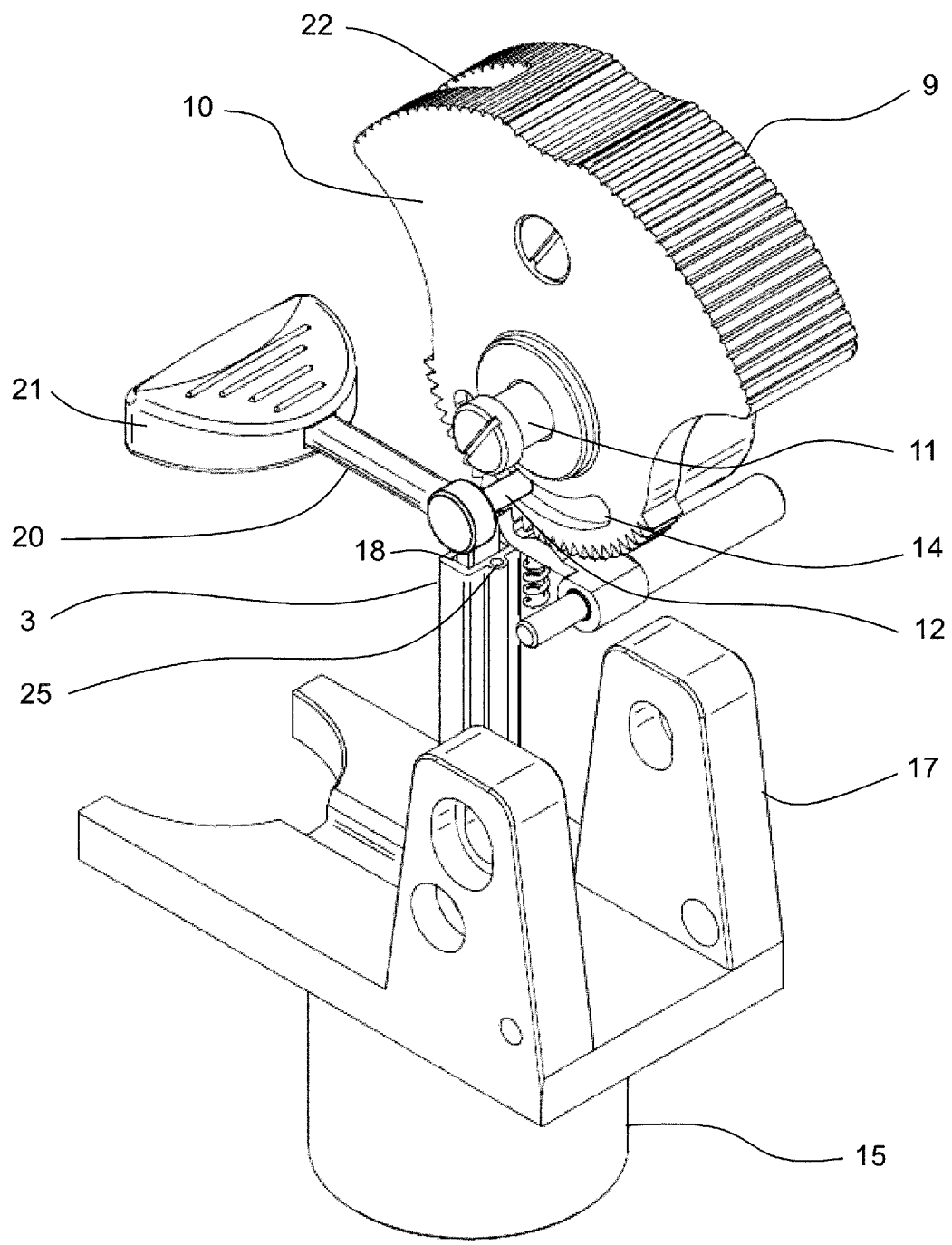
FIG. 4 shows a perspective exploded view of the actuator of FIG. 3.

FIGS. 3 and 4 show respectively a perspective view and an exploded perspective view of an actuator of the stylet of FIGS. 1 and 2, with control wires omitted. FIG. 3 shows the actuator connected to an ET tube connector at attaching portion 15. FIG. 4 does not include an ET tube connector. As described above, the mechanism has a thumb-pad 9 which can be manipulated to provide directional control of the tip of the stylet in a manner described in detail below. The thumb-pad is formed as part of a dial 10 which is rotatable around an axle 11 in response to forces on the thumb-pad provided by an operator. Here, the thumb-pad is shaped to for improved ease of use, including a ridged surface for increased grip by the operator, although this is not essential. The dial is attached to a body or retaining housing 17 of the actuator via the axle 11. Attaching portion 15 is integrally formed with the body of the actuator. This may provide improved ease of manufacture of the device.

The actuator has a sliding pin and slot arrangement having end stops arranged to restrict the movement range of the actuator (and correspondingly restrict the movement range of the stylet tip). Here, the pin 12 is arranged to project from the actuator body 17 to engage slot 14 formed in the dial 10 of the actuator. As the actuator dial is rotated, the slot moves in relation to the pin until the pin hits an end of the slot, preventing further relative movement of the components.

A handle portion 20 of a malleable titanium rod 19 is visible, the remainder of the rod being removably disposed within a central lumen 18 of the tubular stylet body 3. The malleable rod here has a rectangular cross section, with the central lumen of the stylet body being correspondingly rectangular. The handle has a ridged gripping portion 21 to aid removal and insertion of the rod. Here the handle portion of the rod lies within a recess formed in the body of the actuator, which can prevent the handle from obstructing the actuator during use. In use, the malleable rod can either be removed from the stylet completely, or can be bent into a desired shape to aid in insertion of the stylet and ET tube through vocal cords. In this particular embodiment, the dial of the actuator has a notch 22 which enables the malleable rod to be removed easily without obstruction by the dial.

The stylet further has a port 35 located on the body of the actuator for attachment to an air or oxygen line. The port passes through the actuator body into a cavity defined by the attaching portion 15. Thus, when the stylet is attached to an ET tube via an ET tube connector, air or oxygen can be provided into the ET tube via this port on the stylet. The port may have a ridged outer surface to help retain an oxygen line which is connected to the port.

FIG. 5 shows a sectional view of an actuator of FIGS. 3 and 4. There is a control wire 23 extending round a central drum 24 of the actuator dial and attached to a retaining portion 25 to hold its circumferential position. Turning the drum adjusts the pivot angle of the tip of the stylet. In this embodiment, there is a single control wire which is attached to the retaining portion at its centre, thus providing a first control wire portion and a second control wire portion which extend down to opposing sides of the pivotable tip, as shown in FIGS. 6(a) and (b). As the dial of the actuator is rotated, tension is applied to one or other of the two wire portions. By applying tension to the first wire portion, the tip can be moved in a first direction. By applying tension to the second wire portion, the tip can be moved in a second direction. Whilst here the first and second wire portions are part of a single wire, they may alternatively be two separate control wires, and may be attached to a single retaining portion, or separate respective retaining portions, of the actuator.

Conveniently, the stylet body may have one or more wire retainers 24 formed on the body as shown in FIG. 6 (a). Such retainers can help to hold the control wire(s) flush against the stylet body and avoid snagging of the wires during use. Alternatively or additionally, at least a part of one or more of the wire portions may run inside a channel 25 formed in the stylet body, as shown in FIG. 4.

The dial 10 has a toothed portion 27, the notches of which engage with a spring-loaded detent 29 to provide a series of incremental stop points. The detent 29 is on an arm pivotable about a pivot axle 31, and affixed to a spring 33 at the opposing end. Accordingly, the detent is biased into engagement with the notches on the dial 10 by the spring force of the spring. As a user rotates the dial 10 to adjust the pivot angle of the stylet tip, this rotational movement of the toothed portion of the dial forces the detent out of engagement with the notches against the spring force, until the detent can click into the subsequent notch. In this way, the mechanism allows for relatively smooth incremental adjustment of the pivot angle of the stylet tip. One further advantage of the particular mechanism shown is that user does not need to continuously provide input to the control mechanism to keep the stylet tip at a desired angle. Once the pivot angle of the tip has been set by rotation of the dial, the detent holds the dial in the selected position until it is again adjusted by the user. This means that the user can let go of the actuator to perform other actions as needed.

FIGS. 7 (a-c) show a first embodiment of an ET tube 100. The ET tube has a body 101 which comprises a flexible hollow tube. The ET tube body may typically be made from e.g. PVC, although the skilled person will be aware of a range of other suitable materials. The distal end of the tube is inserted into a patient's trachea during intubation. The proximal end of the ET tube may be removably attached to an ET tube connector for connection to a ventilation system, although this is not shown in these drawings. The ET tube has a bending portion 103 located towards the distal end 102 of the body, intermediate the body and the distal tip portion 104 of the tube. The bending portion is here formed as a concertina portion of the tube to promote preferential bending at that position. The concertina allows for increased bending of the bending portion in comparison to the general flexibility of the body of the ET tube, as demonstrated in FIG. 7 (c). The length of the concertina portion is not particularly limited, but should allow a suitable range of angular movement at the bending portion without excessive strain in the material. The position of the bending portion along the length of the ET tube is selected in this embodiment such that when used in combination with the stylet described above, the pivot hinge of the stylet will align with the bending portion of the ET tube.

The ET tube includes two Murphy eyes 105 formed at the distal end of the tube, on opposing sides of the tube. These openings provide alternative flow paths for air in the cause of occlusion of the main outlet of the tube. The Murphy eyes are sized to limit or prevent protrusion of a stylet through the openings.

The skilled person will be well aware of a wide variety of features which the ET tube may incorporate but which are not pictured here, including but not limited to an inflatable cuff and corresponding inflation line with pilot balloon, a radio opaque line to enhance imaging of the tube, and markings on the tube to guide positioning of the tube.

Figure 8:
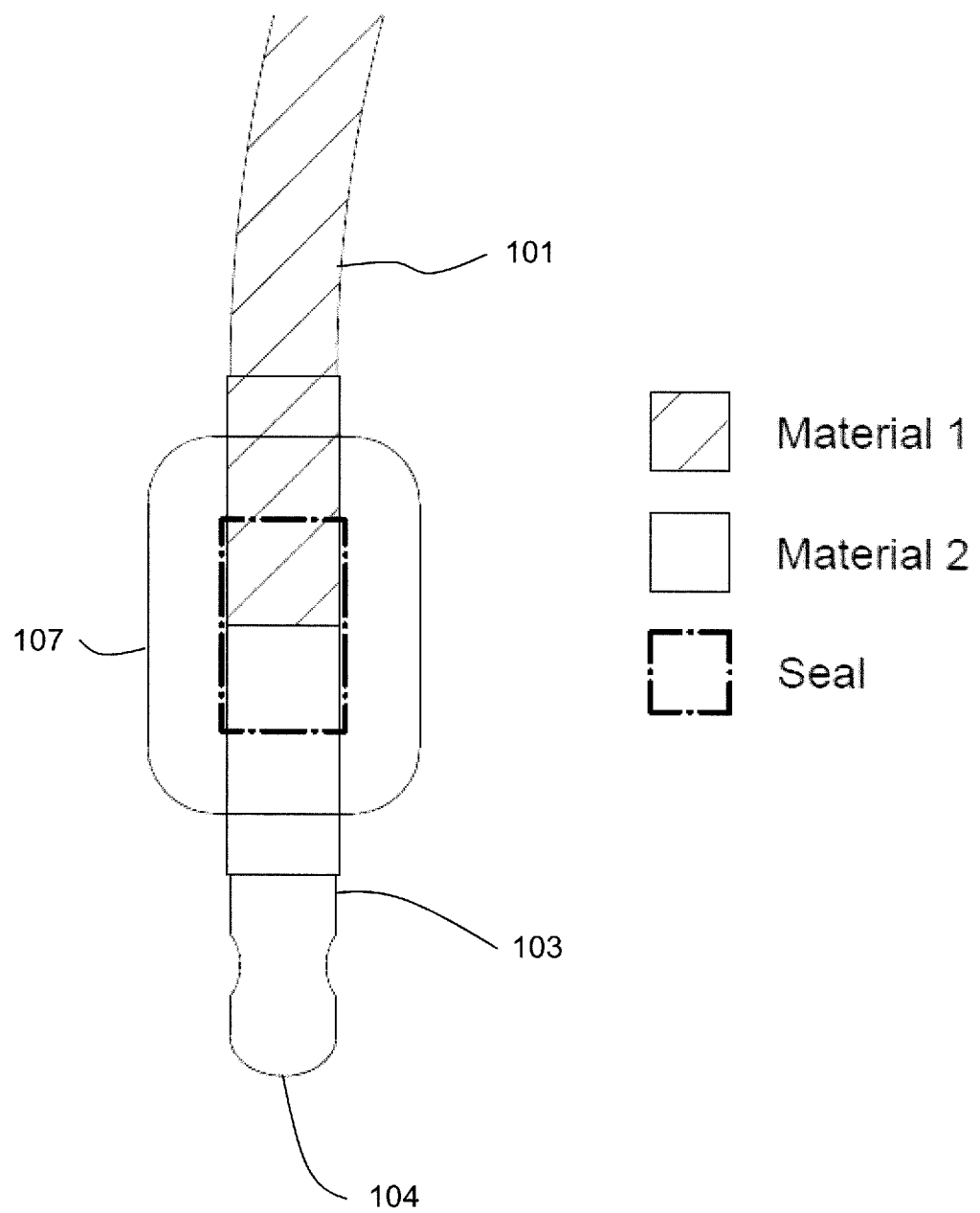
FIG. 8 shows a schematic view of a second embodiment of an ET tube.

FIG. 8 shows a schematic view of a second embodiment of an ET tube. In this embodiment, the bending portion 103 is a portion of the tube made from a different material to the material of the body 101 of the tube. Here, the body of the tube is made from a first type of PVC, and the bending portion is made from a second, softer PVC, although it may also be possible to use e.g. silicone. The body and the bending portion are connected together using a seal (shown as a dashed rectangle) which extends across the join between these portions. The material chosen for the bending portion should typically be more flexible than the material of the body of the ET tube, to allow increased ease of bending the bending portion compared to the body of the ET tube. In this embodiment, the bending portion 103 includes the distal tip portion 104 of the ET tube.

In this particular embodiment, an inflatable cuff 107 is also shown. Such a cuff is a standard feature of many well-known ET tube designs, and as such, the size and shape of the cuff is not particularly limited. Furthermore, the material which the inflatable cuff is made from is not particularly limited and the skilled person will be well aware of a number of suitable materials which could be used for this purpose.

In alternative embodiments, the bending portion may not be formed of a different material, but may be made of the same material having a lower density than the body of the ET tube. Alternatively or additionally, the bending portion may be locally thinned for increased flexibility. It is also considered that any of the above proposed features of the bending portion may be used in combination. The bending portion may be, for example:
 a concertina portion formed from a different material to the material of the ET tube body;
 a locally thinned portion formed of a different material to the material of the body;
 a locally thinned concertina portion; etc.

FIGS. 9 and 10 show views of an intubation kit, including a stylet of the first aspect and an ET tube of the second aspect, in addition to an ET tube connector 200. The ET tube shown here is an ET tube having a concertina bending portion. In FIG. 8, the ET tube is shown as a dashed line. In this figure, it can be seen that the ET tube fits onto the tapered portion 201 of the ET tube connector. Furthermore, the position of the stylet inside the tube can be visualised. Here, the location of the bending portion 103 is selected to align with the location of the pivot hinge 13 of the stylet when the stylet and the ET tube are connected. Typically, the length of the stylet and ET tube respectively will be selected such that the stylet does not protrude from the end of the ET tube when the ET tube is connected to the stylet. This is because where the stylet protrudes from the end of the ET tube, there is a risk that it could cause damage to a patient's airway during the intubation due to the more rigid nature of the stylet (in particular, any rigid elements at the stylet tip) in comparison to the ET tube.

Figure 11:
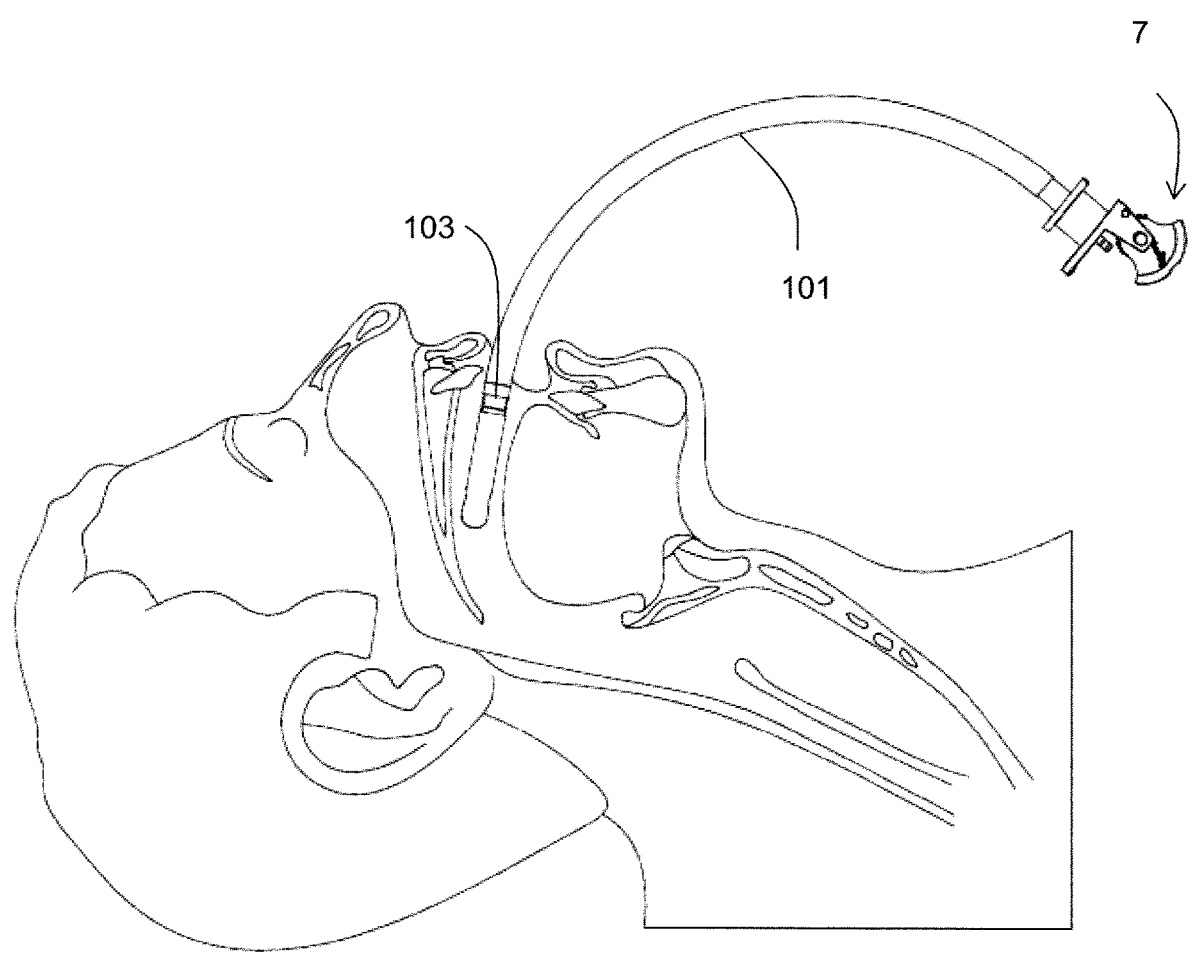
FIG. 11 is a schematic view of the kit in use.

FIG. 11 shows a schematic view of the intubation kit of FIG. 10 in use in an intubation process. As can be seen from the drawing, the ET tube body 101 is generally flexible along its length and can curve to fit the patient's airway. The additional flexibility provided by the bending portion 103 of the ET tube allows for ease of manipulation of the distal end of the ET tube using the pivotable stylet tip, which is controlled by a user using the actuator 7 of the stylet which remains outside of the patient's body during use. Due to the location of the image acquisition device in the stylet tip, the user can more easily guide the ET tube into the desired location by visualisation of the airway from the distal end of the ET tube.

The kit can be used to perform an intubation process, including steps of a) inserting the stylet into the ET tube, b) inserting the stylet and ET tube into the airway of a patient, c) visualising the airway of the patient using the image acquisition device disposed on the stylet tip, d) guiding the ET tube and stylet through the vocal cords of the patient into the trachea of the patient, and e) removing the stylet from the ET tube.

While the invention has been described in conjunction with the exemplary embodiments described above, modifications and variations will be apparent to those skilled in the art. Various changes to the described embodiments may be made without departing from the general teachings herein.

What is claimed is:

1. A stylet device comprising:
   an elongate stylet having a proximal end, a pivoting or hinged location, a distal portion that extends distally from the pivoting or hinged location and a proximal portion that extends proximally from the pivoting or hinged location;
   a rod-receiving lumen having a non-circular cross-sectional configuration and extending from the proximal end of the stylet into said proximal portion;
   a malleable rod having a non-circular cross sectional configuration which corresponds to the non-circular cross sectional configuration of the rod-receiving lumen to deter rotation of the malleable rod within the rod-receiving lumen;
   said malleable rod being alternately insertable through said proximal end and into the rod-receiving lumen and removable through said proximal end from the rod-receiving lumen;
   said pivoting or hinged location being configured to pivot or bend in a manner that allows the distal portion to deflect in at least first and second opposing directions relative to a neutral position without concurrent change in configuration of the proximal portion; and
   a control mechanism useable to cause said deflection of the distal portion.

2. A stylet device according to claim 1 wherein the pivoting location comprises a hinge.

3. A stylet device according to claim 1 wherein the distal portion is alternately deflectable to deflection angles of a) at least 10 degrees in a first direction relative to a neutral or rest position and b) at least 10 degrees in a second direction relative to a neutral or rest position.

4. A stylet device according to claim 1 wherein the control mechanism comprises an actuator located at the proximal end of the stylet.

5. A stylet device according to claim 4 wherein the actuator comprises a rotatable, pivotable or slidable control portion.

6. A stylet device according to claim 4 wherein the actuator comprises a wheel, dial, lever or joystick.

7. A stylet device according to claim 4 wherein the actuator is connected to the distal potion one or more control connectors which is/are moveable to cause said deflection of the distal portion.

8. A stylet device according to claim 7 wherein the actuator comprises at least one line or wire.

9. A stylet device according to claim 8 wherein said at least one line or wire runs through at least one channel formed in the stylet.

10. A stylet device according to claim 8 further comprising one or more retainer(s) for retaining said at least one line or wire.

11. A stylet device according to claim 8 wherein said at least one line or wire comprises a first line or wire segment and a second line or wire segment configured such that application of tension to the first line or wire segment causes the distal portion to deflect in the first direction and application of tension to the second line or wire segment causes the distal portion to deflect in the second direction.

12. A stylet device according to claim 11 wherein the first and second flexible line or wire segments are parts of a single line or wire.

13. A stylet device according to claim 11 wherein the first line or wire segment is separate from the-second line or wire.

14. A stylet device according claim 1 wherein the control mechanism has a plurality of discrete stopping points which provide locking of the distal portion at discrete incremental deflection angles.

15. A stylet device according to claim 1 wherein the tip can be set and locked at a deflection angle which is then maintained during subsequent use of the device without requiring further interaction by an operator.

16. A stylet device according to claim 1 wherein the non-circular cross-section of the malleable rod is oblong.

17. A stylet device according to claim 1 wherein a handle is formed on a proximal end of the malleable rod to facilitate its insertion into and withdrawal from the rod-receiving lumen.

18. A stylet device according to claim 1 further comprising an attaching portion, located at the proximal end of the stylet body, said attaching portion being configured to attach to an endotracheal tube connector.

19. A stylet device according to claim 18 wherein the attaching portion is integrally formed with a body of the actuator.

20. A stylet device according to claim 1 further comprising an air or oxygen port for connection to an air or oxygen line.

21. A stylet device according to claim 1 further comprising an image acquisition device for imaging an area selected from: an area along the longitudinal axis of the tip, an area distal to the tip; an area at an end of an endotracheal tube; and an area located radial to a longitudinal axis of the stylet.

22. A stylet device according to claim 21 wherein the image acquisition stylet device comprises a charge coupled image sensor or other digital image sensor.

23. A system comprising a stylet device according to claim 1 in combination with an endotracheal tube;
   wherein the endotracheal tube has a bending region, a proximal portion located proximal to the bending region and a distal portion located distal to the bending region;
   wherein the stylet device is insertable into the endotracheal tube to a position where the pivoting or hinged location of the stylet device is within the bending region of the endotracheal tube and deflection of the distal portion of the stylet device will cause concurrent deflection of the distal portion of the endotracheal tube without concurrent change in configuration of the proximal portion of the stylet device or the proximal potion of the endotracheal tube.

24. A system according to claim 23 wherein the bending region has a corrugated configuration.

25. A system according to claim 24 wherein the bending region comprises a concertina or accordion segment.

26. A system according to claim 23 wherein the endotracheal tube has a wall and wherein the wall within the bending region is thinner than the remainder of the endotracheal tube wall.

27. A system according to claim 23 wherein the bending region is made from a different material from the remainder of the endotracheal tube.

28. A system according to claim 23 wherein the endotracheal tube further comprises an inflatable cuff.

29. A system according to claim 23 wherein the stylet device further comprises an image acquisition device for imaging an area selected from: an area along the longitudinal axis of the tip; an area distal to the tip; an area at an end of an endotracheal tube; and an area located radial to a longitudinal axis of the stylet.

30. A method for using a system according to claim 23 for endotracheal intubation of a patient airway, said method comprising the steps of:
trans-orally or trans-nasally inserting the endotracheal tube, with the stylet device inserted in the endotracheal tube at said position where the pivoting or hinged location of the stylet device is within the bending region of the endotracheal tube;
advancing the endotracheal tube and stylet to a location where the distal portion of the endotracheal tube is within an oropharynx of the patient;
using the control mechanism to cause deflection of the distal portion of the stylet device and concurrent deflection of the distal portion of the endotracheal tube without concurrent change in configuration of the proximal portion of the stylet device or the proximal portion of the endotracheal tube;
advancing the endotracheal tube through true vocal chords of the patient and into the trachea of the patient;
removing the stylet device; and
ventilating the patient through the endotracheal tube.

31. A method according to claim 30 wherein the stylet device further comprises an image acquisition device and wherein the method further comprises the step of:
using the image acquisition device to visualize a portion of the patient airway.

32. A method according to claim 31 wherein the image acquisition device is used for visualization of the vocal cords and for visualization of a trachea of a patient as the endotracheal tube passes through the vocal cords.

33. A method according to claim 30 wherein the stylet device further comprises an air or oxygen port for connection to an air or oxygen line and wherein the method further comprises connecting said air or oxygen port to a source of air or oxygen thereby causing air or oxygen to be delivered through the endotracheal tube while the stylet device is positioned within the endotracheal tube.

34. A method according to claim 30 wherein the method further comprises the steps of:
inserting the malleable rod into the rod-receiving lumen; and
bending the endotracheal tube, proximal portion of the stylet and malleable rod to a curved shape, causing the malleable rod to deform and thereby maintain that curved shape.

35. A method according to claim 34 wherein the endotracheal tube, stylet and malleable rod are inserted trans-orally.

36. A method according to claim 30 wherein the endotracheal tube and stylet are inserted either trans-nasally or through an intubating oropharyngeal airway or through a supraglottic airway device, without the malleable rod being inserted in the rod-receiving lumen.

* * * * *